United States Patent [19]
Sarris et al.

[11] Patent Number: 5,728,377
[45] Date of Patent: Mar. 17, 1998

[54] METHODS AND COMPOSITIONS INCORPORATING IP-10

[75] Inventors: Andreas H. Sarris, Houston, Tex.; Hal E. Broxmeyer, Indianapolis, Ind.; Jeff V. Ravetch, New York, N.Y.

[73] Assignees: Board of Regents, The University of Texas System, Austin, Tex.; Indiana University Foundation, Bloomington, Ind.; Sloan-Kettering Institute for Cancer Research, New York, N.Y.

[21] Appl. No.: 94,851

[22] Filed: Jul. 20, 1993

[51] Int. Cl.$^6$ ............................................. A61K 45/05
[52] U.S. Cl. ...................... 424/85.1; 435/69.5; 530/351
[58] Field of Search ........................ 424/85.1; 435/69.5; 530/351; 935/13

[56] References Cited

FOREIGN PATENT DOCUMENTS

WO 93/13206  7/1993  WIPO.

OTHER PUBLICATIONS

Chen et al., "Carbohydrate Variant of the Recombinant β–Subunit of Human Choriogonadotropin Expressed in Baculovirus Expression System," *The Journal of Biological Chemistry*, 266(7):4081–4087, 1991.

Chen and Bahl, "Recombinant Carbohydrate Variant of Human Choriogonadotropin β–Subunit (hCGβ) Descarboxyl Terminus (115–145)," *The Journal of Biological Chemistry*, 266(10):6246–6251, 1991.

Chiou and Wu, "Expression of Human Granulocyte–Macrophage Colony–Stimulating Factor Gene in Insect Cells by a Baculovirus Vector," *FEBS Letters*, 259(2):249–253, 1990.

Chua and Blomberg, "Immunochemical Studies of Thylakoid Membrane Polypeptides for Spinach and *Chlamydomonas reinhardtii*," *The Journal of Biological Chemistry*, 254:215–223, 1979.

Davidson and Castellino, "Asparagine–Linked Oligosaccharide Processing in Lepidopteran Insect Cells. Temporal Dependence of the Nature of the Oligosaccharides Assembled on Asparagine–289 of Recombinant Human Plasminogen Produced in Baculovirus Vector Infected *Spodoptera frugiperda* (IPLB–SF–21AE) Cells," *Biochemistry*, 30:6165–6174, 1991.

Dimitriadis, "Effect of Detergents on Antibody–Antigen Interaction," *Analytical Biochemistry*, 98:445–451, 1979.

Gillespie et al., "Expression of Biologically Active Human Antithrombin III by Recombinant Baculovirus in *Spodoptera frugiperda* Cells," *The Journal of Biological Chemistry*, 266(6):3995–4001, 1991.

Ingley et al., "Production and Purfication of Recombinant Human Interleukin–5 from Yeast and Baculovirus Expression Systems," *Eur. J. Biochem.*, 196:623–629, 1991.

Jarvis and Summers, "Glycosylation and Secretion of Human Tissue Plasminogen Activator in Recombinant Baculovirus–Infected Insect Cells," *Molecular and Cellular Biology*, 9(1):214–223, 1989.

Lebacq–Verheyden et al., "Posttranslational Processing of Endogenous and of Baculovirus–Expressed Human Gastrin– Releasing Peptide Precursor," *Molecular and Cellular Biology*, 8(9):3129–3135, 1988.

Luckow and Summers, "High Level Expression of Non-fused Foreign Genes with *Autographa californica* Nuclear Polyhedrosis Virus Expression Vectors," *Virology*, 170:31–39, 1989.

Luster et al., "γ–Interferon Transcriptionally Regulates an Early–Response Gene Containing Homology to Platelet Proteins," *Nature*, 315(6021):672–676, 1985.

Miyajima et al., "Use of the Silkworm, *Bombyx mori*, and an Insect Baculovirus Vector for High–Level Expression and Secretion of Biologically Active Mouse Interleukin–3," *Gene*, 58:273–281, 1987.

Nakhai et al., "The α Subunith of Human Chorionic Gonadotropin Hormone Synthesized in Insect Cells using a Baculovirus Vector is Biologically Active," *FEBS Letters*, 283(1):104–108, 1991.

Quelle et al., "High–Level Expression and Purification of a Recombinant Human Erythropoietin Produced Using a Baculovirus Vector," *Blood*, 74(2):652–657, 1989.

Rodewald et al., "Production of Murine Interleukin–4 and Interleukin–5 by Recombinant Baculovirus," *Journal of Immunological Methods*, 132:221–226, 1990.

Sarris et al., "Recombinant Human IP–10: Expression, Biochemical Characterization, Purification and Inhibition of Early Human Hematopoietic Progenitors," *ISEH*, 1993, Abstract only.

Smith et al., "Production of Human Beta Interferon in Insect Cells Infected with a Baculovirus Expression Vector," *Molecular and Cellular Biology*, 3(12):2156–2165, 1983.

Smith et al., "Modification and Secretion of Human Interleukin 2 Produced in Insect Cells by a Baculovirus Expression Vector," *Proc. Natl. Acad. Sci. USA*, 82:8404–8408, 1985.

Steiner et al., "Human Tissue–Type Plasminogen Activator Synthesized by Using a Baculovirus Vector in Insect Cells Compared with Human Plasminogen Activator Produced in Mouse Cells," *Gene*, 73:449–457, 1988.

Whitefleet–Smith et al., "Expression of Human Plasminogen cDNA in a Baculovirus Vector–Infected Insect Cell System," *Archives of Biochemistry and Biophysics*, 271(2):390–399, 1989.

(List continued on next page.)

*Primary Examiner*—Toni R. Scheiner
*Attorney, Agent, or Firm*—Arnold, White & Durkee

[57] ABSTRACT

The present invention discloses the correct processing of IP-10, a myelosuppressive protein produced by certain cells such as keratinocytes, monocytes and human endothelial cells upon stimulation by γ-interferon. Also disclosed is a method of treating human cancer patients by applying IP-10 in a pharmaceutical composition in conjunction with certain antineoplastic agents.

15 Claims, 6 Drawing Sheets

OTHER PUBLICATIONS

Wojchowski et al., "Active Human Erythropoietin Expressed in Insect Cells Using a Baculovirus Vector: A Role for N-Linked Oligosaccharide," *Biochimica et Biophysica Acta*, 910:224–243, 1987.

Dewald et al., "IP-10, a γ-Interferon-inducible Protein Related to Interleukin-8, Lacks Neutrophil Activating Properties," *Immunology Letters*, 32:81–84, 1992.

Luster and Leder, "IP-10, a –C–X–C Chemokine, Elicits a Potent Thymus-dependent Antitumor Response In Vivo," *J. Exp. Med.*, 178:1057–1065, 1993.

Narumi et al., "Tissue-specific Expression of Murine IP-10 mRNA Following Systemic Treatment with Interferon γ," *Journal of Leukocyte Biology*, 52(1):27–33, 1992.

Ohmori and Hamilton, "A Macrophage LPS-Inducible Early Gene Encodes the Murine Homologue of IP-10," *Biochemical and Biophysical Research Communications*, 168(3):1261–1267, 1990.

Smoller and Krueger, "Detection of Cytokine-induced Protein γ-Immune Protein-10 (γ-IP10) in Atypical Melanocytic Proliferations," 25(4):627–631, 1991.

Broxmeyer, et al "Synergistic Suppressive Interactions of Human Chemokines on Human Myeloid Progenitor Cell Proliferation", Molecular Biology of Hematopoiesis 8th Symposium, Basel, Switzerland, Jul. 9–13, 1993, Abstract only.

Broxmeyer et al J of Immun. 150(8): 3448–4458 (Apr. 15, 1993).

Luster et al J of Exp Med. 166: 1084–1097, 1987.

Oppenheim *The Chemokines*, 1993, pp. 183–186.

Luster et al J of Ex Med 166: 1098–1108, 1987.

Luster et al, Keystone Symposia Jan./Feb. 1993, p. 121.

Harlow et al In *Antibiotics, A Lab. Manual*, Cold Spring Harbor Lab. 1988, pp. 285 and 287.

METHODS AND COMPOSITIONS INCORPORATING IP-10

BACKGROUND OF THE INVENTION

1. Field of the Invention

The present invention relates generally to the field of the myelosuppressive action of a family of proteins that are secreted by certain types of cells in response to γ-interferon (γ-IFN), and more particularly to the myelosuppressive action of that protein known as IP-10, which is secreted by human keratinocytes, monocytes and endothelial cells.

2. Description of the Related Art

The cellular immune response is characterized by the complex interaction of many different cells responding to multiple extracellular signals. Activation, proliferation, and directed migration of both local and blood-borne cells is partly regulated by soluble mediators released by cells, referred to collectively as cytokines. One family of these proteins includes the interferons, a group of proteins first identified by their ability to induce cellular resistance to infection by many viruses. γ-IFN, a glycoprotein secreted from activated T cells, has potent immunomodulatory activities and is an important activator of the cellular immune response. In addition to the antiviral properties it shares with the α- and β- interferons, γ-IFN also activates macrophages and stimulates B cells.

IP-10 is a protein secreted by keratinocytes, monocytes and human endothelial cells after stimulation by recombinant γ-IFN. The gene encoding IP-10 has previously been cloned (Luster et al., 1985, Luster et al., 1987). DNA sequence analysis has demonstrated that IP-10 belongs to the intercrine cytokine or chemokine family of proteins (Wolpe et al., 1989; Oppenheim et al., 1991), so named for their chemotactic activity towards neutrophils, monocytes, T cells, basophils and fibroblasts. Some chemokines inhibit early subsets of bone marrow progenitors (Graham et al., 1990; Broxmeyer et al., 1990; Broxmeyer et al., 1991; Dunlop et al., 1992; Lord et al., 1992; Maze et al., 1992; Broxmeyer et al., 1993). This family is divided into two subgroups based on the arrangement of the first two of four conserved cysteines: the α-subfamily with the C—X—C motif, which is located on human chromosome 4 (q12–21) and includes GRO-α, β-thromboglobulin, MIP-2α, MIP-2β, IL-8, NAP-2, and IP-10; and the β-subfamily with the C—C motif, which is located on human chromosome 17 (q11–32) and includes MIP-1α, MIP-1β, MCAF, and RANTES (Wolpe et al., 1989; Oppenheim et al., 1991).

Even though recombinant IP-10 has been expressed and the purified recombinant protein has been available, no practical usefulness for IP-10 has been reported. On the contrary, previous attempts to demonstrate a biological function for IP-10 have been unsuccessful (Dewald et al., 1992). Furthermore, the final processed form of IP-10 has not been known, rendering uncertain the preparation of appropriate recombinant vectors and recombinant protein for further study of the biological function of this protein. Therefore, since so little is known about the biological function of IP-10, there is a continuing need in the art to characterize, understand and ultimately exploit the activity of this protein.

SUMMARY OF THE INVENTION

The present invention involves, in a general and overall sense, the discovery by the inventors that IP-10 directly inhibits the growth of early bone marrow or hematopoietic progenitors and thus can be employed in a variety of embodiments, including clinical compositions and methods. Most importantly, in that the present inventors herein demonstrate that IP-10 can inhibit proliferation of early human bone marrow myeloid progenitors, it is envisioned that IP-10 can be employed to protect such cells from the adverse effects of agents that selectively exert a cytotoxic effect upon normal, dividing bone marrow progenitors.

While many cancer cell types are characterized by uncontrolled growth characteristics, there have been few other cancer-specific biological or cellular targets for the development of directed chemotherapy. Accordingly, most traditional cancer therapies are very nonspecific in that they employ antineoplastic agents that indiscriminantly kill rapidly growing cells and cell types, whether cancerous or not. The most susceptible normal tissues to the ravaging effects of chemotherapy are thus rapidly growing cell types such as bone marrow progenitor cells and cells of the gastrointestinal tract. The present invention thus embodies distinct advantages as, through the administration of pharmaceutical compositions of IP-10, it is proposed that one can induce a non-dividing state in hematopoietic progenitor cells, protecting them from the anticellular effects of cell cycle specific agents, such as hydroxyurea, cytosine arabinoside, methotrexate and vincristime.

The inventors also contemplate that IP-10 may have utility as a direct inhibitor of tumor cell growth. While the effect of IP-10 upon leukemic cells is presently unknown, it may exert a direct inhibitory effect upon sarcomas such as Kaposi's sarcoma, by virtue of its similarity to Platelet Factor 4, which is active against Kaposi's sarcoma in AIDS patients (Kahn et al., 1993). In connection with the treatment of Kaposi's sarcoma, it is contemplated that IP-10 may be particularly useful because as presently employed, it does not promote HIV replication. Similarly, with respect to the treatment of leukemia patients, IP-10 may ultimately demonstrate strong inhibitory effects against leukemic stem cells that are known to depend on steel factor. It is proposed that in these patients IP-10 can be employed directly as an anti-leukemic agent. In patients wherein IP-10 does not inhibit leukemic cells, it can be employed in the treatment of leukemia as an adjunct to traditional chemotherapy as discussed above, because it will protect normal bone marrow stem cells, but not leukemic cells.

Accordingly, it can be appreciated that the present invention involves, in certain more general embodiments, methods for inhibiting the growth of early hematopoietic progenitor cells. Such methods include contacting a population of cells that include hematopoietic progenitor cells with an effective amount of IP-10. Effective amounts of IP-10 will be those quantities of IP-10 which are effective to inhibit early hematopoietic progenitor cell growth, as exemplified herein. While it is generally believed that IP-10 will prove useful in inhibiting all such early progenitor cells, the cells typically observed to be inhibited by recombinant IP-10 ("rIP-10") include early subsets of granulocyte-macrophage progenitor cells (CFU-GM), multipotential (CFU-GEMM) and erythroid (BFU-E) progenitors that depend on rSLF in addition to rGM-CSF or rEPO respectively.

Surprisingly, inactive concentrations of rIP-10 combined with inactive concentrations of rMIP-1α, rMIP-2α, PF4, rIL-8, or rMCAF have been found to result in synergistic inhibition of early progenitors. Therefore, further aspects of the present invention include compositions comprising IP-10, such as rIP-10, which may or may not have activity individually, in combination with any one or more of rMIP-1α, rMIP-2α, PF4, rIL-8, or rMCAF, at concentrations which may or may not have activity individually.

In preferred aspects, the invention concerns the generation and use of recombinant IP-10 which is produced through the application and use of recombinant DNA segments comprising the IP-10 gene (see Luster et al., 1985 and Luster et al., 1987). It is proposed that any method for recombinant production will be suitable for use in connection with the present invention. However, an aspect of the invention is the inventors' discovery of the correct structure of the active, naturally secreted form of IP-10, which is initially produced with a 21 amino acid leader sequence that is cleaved off during secretion, leaving the so-called f(22–98) (IP-10 fragment composed of amino acids 22–98) as the active, secreted form of the protein.

Thus, if one envisions employing a bacterial recombinant expression system such as E. coli, it will be appropriate to prepare a vector construct that will directly encode and thereby produce f(22–98) IP-10. This is because bacterial expression systems will be unable to remove that leader sequence from the finished protein. However, where a eukaryotic recombinant cell expression system such as an insect cell or a mammal or even a human cell is employed, one will not be required to prepare a truncated IP-10 expression segment in that the host system itself will remove the leader sequence of 21 amino acids (assuming that the cDNA encoding the full length, secreted form of IP-10 is employed).

Certain aspects of the present invention therefore concern methods for inhibiting the growth of hematopoietic progenitor cells which include preparing recombinant IP-10 (rIP-10) and contacting a composition containing such cells with an effective amount of rIP-10. rIP-10 may be prepared by any suitable process, such as, e.g., by preparing a recombinant host cell which includes a recombinant gene segment encoding IP-10, culturing the cell under conditions effective to allow the expression of the gene so that the recombinant protein is produced and collecting and purifying the IP-10 so produced.

It is understood that the recombinant IP-10 may be produced in a bacterial or prokaryotic cell, or in an insect, animal or human cell. Collecting the IP-10 may take the form of collecting media or 'conditioned media' surrounding the recombinant cells, or may include first lysing or otherwise breaking the cells and generally removing any cell debris. Various techniques are suitable for use in protein purification, virtually any of which may be employed to purify recombinant IP-10. These include, but are not limited to: precipitation, e.g., using salt, antibodies, ammonium sulphate, PEG, and the like, followed by centrifugation; chromatography steps such as ion exchange, gel filtration and reverse phase chromatography, any of which may also be used with FPLC and HPLC, and also hydroxylapatite and affinity chromatography; isoelectric focusing; gel electrophoresis including SDS-PAGE and gel-elution; and combinations of such and other techniques known to those of skill in the art. The preferred method for purifying IP-10 disclosed herein involves immunoprecipitation and affinity chromatography and represents the best mode presently known by the inventors to prepare substantially purified IP-10.

The inventors contemplate that the purified IP-10 so produced may be comprised in a pharmaceutical composition and that the said pharmaceutical composition may be administered to a human cancer patient. This administration of IP-10 may be followed by the administration of an anti-neoplastic agent which is toxic to bone marrow cells and which is administered in a therapeutically effective amount. Therefore, a certain embodiment of the present invention comprises an improved method for chemotherapy of a cancer patient employing an antineoplastic agent having bone marrow toxicity, wherein the improvement comprises treating said patient with an early hematopoietic progenitor cell inhibitory amount of IP-10.

Pharmaceutical compositions in accordance with the present invention may therefore include purified IP-10, and preferably rIP-10; or rIP-10 in combination with another beneficial agent, such as a cytokine; or rIP-10 in combination with an anti-neoplastic agent. Anti-neoplastic agents include, but are not limited to alkylating agents; antimetabolites, such as purine and pyrimidine analogs and vinca alkaloids; natural products including antibiotics and miscellaneous agents used in the treatment of various neoplastic diseases. Specific examples of such compounds include doxorubicin, daunomycin, methotrexate, vinblastine, hydroxyurea and cytosine arabinoside.

The improved method for inhibiting the growth of hematopoietic progenitor cells in a patient may comprise the steps of preparing a recombinant host cell comprising a recombinant gene segment encoding IP-10, culturing said cell under conditions effective to allow expression of said gene to produce IP-10; collecting and purifying the recombinant IP-10 so produced; rendering said recombinant IP-10 pharmacologically acceptable; and administering said pharmacologically acceptable IP-10 to said patient in an amount effective to inhibit hematopoietic progenitor cells.

In preferred embodiments, the rIP-10 is produced from a baculovirus expression vector in an insect host cell. The IP-10 may be produced from a recombinant gene segment which encodes f(22–98) or it may encode the entire 98 amino acid sequence of IP-10, or it may be naturally occurring IP-10, derived from stimulated keratinocytes, monocytes or endothelial cells, for example. The IP-10 may be purified and rendered pharmacologically acceptable and sterile as described herein, and as known to those of skill in the art, and administered to a human cancer patient to whom is also administered an agent, an antineoplastic agent for example, having bone marrow toxicity.

It is understood that the IP-10 which is used in the pharmaceutical composition may be prepared by a process that includes preparing a recombinant host cell comprising a recombinant gene segment encoding IP-10; culturing said cell under conditions effective to allow expression of said gene to produce IP-10; and collecting and purifying the IP-10 so produced. The composition will generally comprise from about 99 to about 99.99% IP-10, and more preferably from about 100 to about 200 µg/ml of IP-10.

The inventors' contemplate that the pharmaceutical composition may be prepared by a method comprising the steps of obtaining a composition that includes IP-10; purifying the IP-10 from said composition by removing one or more impurities therefrom; and rendering the purified composition pharmacologically acceptable to provide the pharmaceutical composition. The term "pharmaceutically acceptable" refers to molecular entities and compositions which do not produce an adverse, allergic or other untoward reaction when administered to a human. The preparation of suitable pharmacological compositions is routine to those of skill in the art, as exemplified by "Remington's Pharmaceutical Sciences" 15th Edition, incorporated herein by reference.

The composition that includes IP-10 may be obtained by stimulating keratinocytes, monocytes, endothelial cells or others with an amount of γ-interferon effective to promote the release of IP-10 by said cells, and collecting and partially purifying the IP-10 so released to provide the composition or by preparing a recombinant host cell comprising a recombinant gene segment encoding IP-10; culturing said cell under conditions effective to allow expression of said gene to produce IP-10; and collecting and purifying the IP-10 so produced. The recombinant gene segment may encode f(22–98) IP-10 or it may encode full length IP-10. It is understood that the IP-10 described in this paragraph may be produced from a baculovirus expression vector or by any other means.

BRIEF DESCRIPTION OF THE DRAWINGS

FIG. 1A. Protein synthesis by wild type and recombinant baculoviruses. Cells were pulsed with [$^{35}$S]-methionine from 60 to 66 hours post-infection, washed, boiled in sample buffer and analyzed by SDS-PAGE. The top of each lane designates the infecting baculovirus. WT: wild type baculovirus. Sf9: un-infected cells.

FIG. 1B. Immunoprecipitations of cell-associated rIP-10. Sf9 cells were infected with A221, pulsed with [$^{35}$S]-methionine from 60 to 66 hours post infection, boiled in SDS (T), and immunoprecipitates of an equal number of cells by non-immune serum (NI), anti-IP-10, or anti-22 were analyzed with SDS-PAGE followed by fluorography, as designated at the top of the corresponding lanes. * designates the 11.9 kDa form, and ** the 9.9 kDa form of rIP-10.

FIG. 2A is a duplicate membrane stained with anti-IP-10.

FIG. 2B is a duplicate membrane stained with anti-22.

FIG. 3A. Reverse-phase HPLC of rIP-10 purified from Sf9 cells infected with A221. A$_{230}$ is the optical density of the eluate at 230 nm and % B is the gradient of propanol-acetonitrile-TFA.

FIG. 3B. Analysis of the purification of rIP-10 by SDS-PAGE. S, supernatants of A221-infected Sf9 cells 6 days after infection; F, representative fractions of FPLC on Sepharose-S; H, peak fraction of reverse-phase HPLC shown in 3A; and E, purified f(22–98) from $E.\ coli$.

FIG. 4A. Effect of rIP-10 on CFU-GEMM.

FIG. 4B. Effect of rIP-10 on BFU-E.

FIG. 4C. Effect of rIP-10 on CFU-GM.

DETAILED DESCRIPTION OF THE PREFERRED EMBODIMENTS

Figures 1A, 1B:
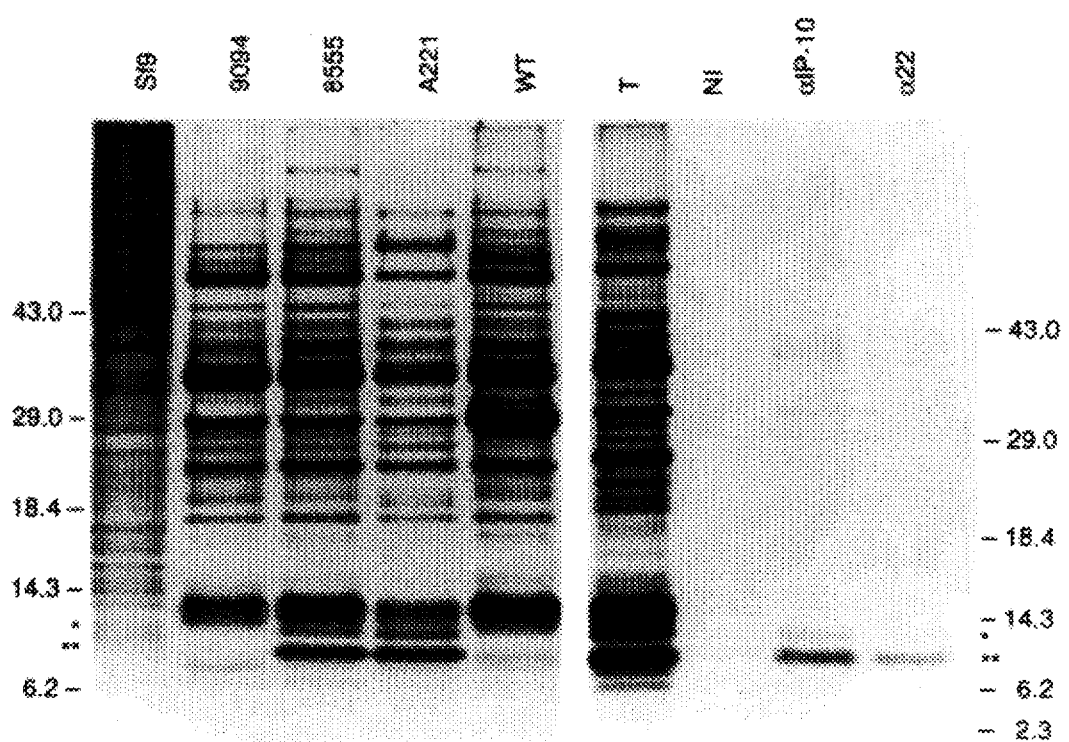
FIGS. 1A and 1B. SDS-PAGE analysis of protein synthesis by various baculovirus vectors.

A particular embodiment of the present invention is the use of a processed, recombinant protein in a pharmaceutical preparation in conjunction with chemotherapy of cancer patients. IP-10, a member of the family of small secreted proteins called intercrine cytokines or chemokines, is secreted by γ-IFN stimulated T cells, monocytes, endothelial cells and keratinocytes. The biological properties of IP-10 can now be explored due to the cloning of the gene and overexpression in baculovirus and in bacterial protein expression systems. A 9.9 kDa protein was secreted by insect cells infected with a baculovirus vector containing the IP-10 gene. The said 9.9 kDa protein co-migrated with keratinocyte IP-10 and with f(22–98), a bacterial recombinant fragment lacking the signal sequence, but containing all other residues of IP-10 on SDS-PAGE. All three polypeptides reacted with antibodies recognizing residues 10–98 (anti-IP-10) and 77–98 (anti-22) of IP-10, demonstrating that IP-10 is secreted by keratinocytes and infected insect cells after removal of the signal sequence. An important discovery of the present invention is the fact that the IP-10 protein does not undergo proteolysis of the carboxy-terminal end as was previously believed. It is the inventors' belief, in fact, that the deletion of the 21 carboxy-terminal residues of IP-10 results in an inactive protein, in direct contradiction of the previous model (Luster and Ravetch, 1987).

Purified rIP-10 suppresses in vitro colony formation by early human bone marrow progenitor cells which need r-Steel Factor (rSLF) and r-granulocyte-macrophage CSF (rGM-CSF) or rSLF and r-erythropoietin (rEPO). The inhibition is dose-dependent, is complete at concentrations ≧50 ng/ml, is prevented by preincubation of rIP-10 with anti-IP-10, but not by anti-22, and is also seen with highly purified CD-34$^{+++}$ cells, suggesting direct effect by rIP-10 on the progenitors. Combinations of rIP-10 and other chemokines at inactive concentrations inhibited colony formation in a synergistic manner. rIP-10 did not affect colony formation in the absence of any growth factors or in the presence of rEPO or rGM-CSF but in absence of rSLF. The effects of IP-10 may be relevant to normal marrow function and might be harnessed to protect human hematopoietic progenitors from the cytotoxic effects of chemotherapy.

Abreviations

The following abbreviations are used throughout the present disclosure:

SLF, steel factor; EPO, erythropoietin; CFU-GM, CFU-granulocyte-macrophage; CFU-GEMM, CFU-granulocyte-erythroid-macrophage-megakaryocytic; BFU-E erythroid burst forming unit; PF4, platelet factor-4; FPLC, fast performance liquid chromatography; MIP, macrophage inflammatory protein; NAP, neutrophil activating peptide; MCAF, macrophage chemotactic and activating factor; IL, interleukin.

Cloning and Protein Purification

A technique often employed by those skilled in the art of protein production today is to obtain a so-called "recombinant" version of the protein, to express it in a recombinant cell and to obtain the protein from such cells. These techniques are based upon the "cloning" of a DNA molecule encoding the protein from a DNA library, i.e., on obtaining a specific DNA molecule distinct from other portions of DNA. This can be achieved by, for example, cloning a cDNA molecule, or cloning a genomic-like DNA molecule.

The first step in such cloning procedures is the screening of an appropriate DNA library, such as, in the present case, a human histiocytic lymphoma cell line. The screening procedure may be an expression screening protocol employing antibodies directed against the protein, or activity assays. Alternatively, screening may be based on the hybridization of oligonucleotide probes, designed from a consideration of portions of the amino acid sequence of the protein, or from the DNA sequences of genes encoding related proteins. After identifying an appropriate DNA molecule, it may be inserted into any one of the many vectors currently known in the art and transferred to a prokaryotic or eukaryotic host cell where it will direct the expression and production of the so-called recombinant version of the protein.

Alternatively, a cDNA library may be constructed from poly (A)$^+$ RNA isolated from cells such as the U937 cell line. This RNA may then be translated in a cell free system such as the rabbit reticulocyte system. The translation products may then be analyzed by SDS-PAGE, for example. It is understood also, that a subtraction hybridization system may be employed to discover mRNA that is only synthesized in response to certain stimuli, γ-IFN, for example.

It will be understood that recombinant IP-10 may differ from naturally-produced IP-10 in certain ways. In particular, the degree of post-translational modifications, such as, for example, glycosylation and phosphorylation may be different between the recombinant IP-10 and the IP-10 purified from a natural source, such as keratinocytes.

Protein Purification

Further aspects of the present invention concern the purification, and in particular embodiments, the substantial purification, of a protein. The term "purified protein" as used herein, is intended to refer to a protein composition, isolatable from total serum protein, wherein the protein is purified to any degree relative to its naturally-obtainable state, i.e., in this case, relative to its purity within a serum extract. A purified protein therefore also refers to a protein, free from the environment in which it may naturally occur.

Various methods for quantifying the degree of purification of the protein will be known to those of skill in the art in light of the present disclosure. These include, for example, assessing the number of polypeptides within a fraction by SDS/PAGE analysis.

The actual units used to represent the amount of inhibitory activity will, of course, be dependent upon the particular assay technique chosen to follow the purification. As discussed below, the present inventors prefer to use an assay based upon the suppression of colony growth of CFU-GM in the presence of rGM-CSF and rSLF; or the inhibition of BFU-E or CFU-GEMM in the presence of rSLF and rEPO.

Generally, "purified" will refer to a protein composition which has been subjected to fractionation to remove various non-protein components or other irrelevant proteins. Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques.

The preferred purification method disclosed hereinbelow contains several steps and represents the best mode presently known by the inventors to prepare a substantially purified IP-10. This method is currently preferred as it results in the substantial purification of the protein, as assessed by colony suppressing activity. This preferred mode of protein purification involves the execution of certain purification steps in the order described hereinbelow. However, as is generally known in the art, it is believed that the order of conducting the various purification steps may be changed, or that certain steps may be omitted, and still result in a suitable method for the preparation of a substantially purified IP-10.

Keratinocyte expression

Primary human keratinocytes were grown in serum-free media (Krueger, 1990), and induced with 500 U/ml rIFN-γ. The supernatant was collected after 24 hours, and concentrated 10-fold with trichloroacetic acid precipitation before western blotting. Keratinocytes were labelled with $^{35}$S-methionine and IP-10 immunoprecipitated from their supernatants as previously described (Luster, 1987; Krueger, 1990).

Recombinant Host Cells and Vectors

Prokaryotic hosts are preferred for expression of the unprocessed IP-10 protein, or for any defined fragment of IP-10. Some examples of prokaryotic hosts are *E. coli* BL21 (DE3) which is particularly useful. Others are *E. coli* LE392, *E. coli* B, *E. coli* RR1, *E. coli* X 1776 (ATCC No. 31537) as well as *E. coli* W3110 (F-, lambda-, prototrophic, ATCC No. 273325), bacilli such as *Bacillus subtilis*, or other enterobacteriaceae such as *Salmonella typhimurium* or *Serratia marcescens*, and various Pseudomonas species may be used.

More particularly, rIP-10 has been produced using the T7 polymerase bacterial expression system (provided by F W Studier, Brookhaven National Laboratories, New York, Studier, 1990). The polymerase chain reaction and appropriate oligonucleotide primers (Saiki, 1988) were used to amplify fragments of IP-10 cDNA with NcoI ends for cloning in the protein expression vector peT-3d. Oligonucleotides were synthesized on a model 380B synthesizer from Applied Biosystems (Foster City, Calif.) using phosphoramidite chemistry. The primers used were OL1075 (GGATCCATGGTACCTCTCTAGAACC; seq id no:1) as the 5' and OL 1076 (GGATCCATGGTTAAGGAGA-TCTTTTAGA; seq id no:2) as the 3' primer. A cDNA coding for f(22–98), a fragment extending from Valine 22 to Proline 98 and lacking the signal sequence of IP-10 was amplified. In order to approximate the previously reported processed form of IP-10 (Luster, 1987), OL1075 was used as the 5' primer and OL1077 (GGATCCATGGTTATGGATTCAGACATCTCTT; seq id no:3) as the 3' primer. This procedure amplified f(22–77), a cDNA coding for a fragment extending from Valine 22 to Proline 77, and lacking both the signal sequence and the last 21 residues of IP-10, but retaining the 4 internal cysteine residues. The PCR products were restriction digested with Nco1 and were cloned into peT-3d, thus removing all residues of the φ10 protein (Studier, 1990), and expressing the IP-10 fragments as nonfusion proteins with an added methionine at the amino terminus. The IP-10 coding regions of the recombinant plasmids were sequenced (Sanger, 1977) to eliminate the possibility of PCR and cloning errors. Recombinant plasmids were transformed into lysogen BL21 (DE3) and transformants were induced with 0.4 mM IPTG (Studier, 1990). Recombinant f(22–98) was solubilized (Marston) and purified as described for neutrophil activating peptide (Lindley, 1988), using 40 mM Na Phosphate pH 7.2 during chromatography in S-Sepharose. Fractions with IP-10 were pooled and dialysed against PBS.

In addition to prokaryotes, eukaryotic microbes, such as yeast cultures may also be used. *Saccharomyces cerevisiae*, or common baker's yeast is the most commonly used among eukaryotic microorganisms, although a number of other strains are commonly available. For expression in Saccharomyces, the plasmid YRp7, for example, is commonly used (Stinchcomb et al., 1979; Kingsman et al., 1979; Tschemper et al., 1980). This plasmid already contains the trpl gene which provides a selection marker for a mutant strain of yeast lacking the ability to grow in tryptophan, for example ATCC No. 44076 or PEP4-1 (Jones, 1977). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., 1980) or other glycolytic enzymes (Hess et al., 1968; Holland et al., 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, an origin of replication, and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (*Tissue Culture*, 1973). Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation site, and transcriptional terminator sequences.

Of particular interest is the baculovirus system in which Sf9 insect cells infected with recombinant baculoviruses synthesize large amounts of recombinant proteins. Of particular importance is the ability of Sf9 cells to remove leader sequences, correctly fold proteins, and secrete them in the media (Webb and Summers, 1990; Summers and Smith, 1987). Many secreted proteins have been successfully produced in soluble, biologically active form from Sf9 cells infected by recombinant baculoviruses (Smith, 1985; Miyajima, 1987; Rodewald, 1990; Ingley, 1991; Smith, 1983; LeBacq-Verheyden, 1988; Whitefleet-Smith, 1989; Davidson, 1991; Steiner, 1988; Jarvis, 1989; Wojchowski, 1987; Quelle, 1989; Barnett, 1990; Chiou, 1990; Nkhai, 1991; Chen, 1991; Chen, 1991; Gillepsie, 1991).

DNA Segments

Important aspects of the present invention concern isolated DNA segments and recombinant vectors encoding the IP-10 protein, and the creation of recombinant host cells, through the application of DNA technology, which express IP-10.

As used herein, the term "DNA segment" is intended to refer to a DNA molecule which has been isolated free of total genomic DNA of a particular species. Therefore, a DNA segment encoding IP-10 is intended to refer to a DNA segment which contains such coding sequences, yet is isolated away from total genomic DNA of the human cell.

Included within the term "DNA segment", are DNA segments which may be employed in the preparation of vectors, as well as the vectors themselves, including, for example, plasmids, cosmids, phage, viruses, and the like.

Recombinant vectors and isolated segments may variously include the IP-10 coding regions themselves, coding regions bearing selected alterations or modifications in the basic coding region or may encode larger polypeptides which nevertheless include sequences which will define the myelosuppressive activity.

Site-Specific Mutagenesis

Site-specific mutagenesis is a technique useful in the preparation of individual peptides, or biologically functionally equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art as exemplified by publications (Adelman et al., 1983). As will be appreciated, the technique may employ a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes the IP-10 protein. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected IP-10 encoding gene using site-directed mutagenesis is provided as a means of producing potentially useful protein species and is not meant to be limiting as there are other ways in which sequence variants of the protein may be obtained. For example, recombinant vectors encoding the desired IP-10 encoding gene may be treated with mutagenic agents to obtain sequence variants (see, e.g., a method described by Eichenlaub, 1979) for the mutagenesis of plasmid DNA using hydroxylamine.

Protein Modifications

As mentioned above, modification and changes may be made in the structure of IP-10 and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules or receptors. Since it is the interactive capacity and nature of a protein that defines that protein's biological functional activity, certain amino acid sequence substitutions can be made in a protein sequence (or, of course, its underlying DNA coding sequence) and nevertheless obtain a protein with like, enhanced or even countervailing properties (e.g., antagonistic v. agonistic). It is thus contemplated by the inventors that various changes may be made in the sequence of IP-10 proteins or peptides (or underlying DNA) without appreciable loss of their biological utility or activity, and changes may also be made which enhance their biological utility or activity.

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant protein, which in turn defines the interaction of the protein with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. For example, site specific mutagenesis of phenylalanine 56 of IP-10 to tyrosine may permit the generation of a biologically active molecule able to bind on the surface of early hematopoietic progenitors or appropriate cell lines. The tyrosine can be labeled with radioactive iodine without destroying the biological activity of the protein, and thus would allow the study and isolation of the cellular receptors of IP-10.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

In addition, deletion mutations of IP-10 can be generated with the polymerase chain reaction, as is the case of f(22–77) which lacks the last 21 carboxy-terminal residues of IP-10 and is believed to be inactive. This discovery enhances the value of the correct definition of the natural form of IP-10 contained within the present disclosure.

Pharmaceutical Preparations

The novel pharmaceutical preparations of the present invention may be administered alone or in combination with pharmaceutically acceptable carriers, in either single or multiple doses. Suitable pharmaceutical carriers include inert solid diluents or fillers, sterile aqueous solution and various organic solvents. The pharmaceutical compositions formed by combining a protein of the present invention and the pharmaceutically acceptable carriers are then easily administered in a variety of dosage forms such as injectable solutions.

For parenteral administration, solutions of the protein in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils.

The proper fluidity can be maintained, for example, by the use of a coating, such as lecithin, by the maintenance of the required particle size in the case of dispersion and by the use of surfactants. It is also contemplated that dilute acidic solutions may be preferred in order to maintain IP-10 in solution. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Suppression of Stem Cells During Chemotherapy

In a certain embodiment, the myelosuppressive activity of the pharmaceutical preparations discussed above may prove useful in the treatment of human cancers. For example, chemotherapeutic agents are often designed to have a selective effect on rapidly growing cells. Unfortunately, healthy bone marrow, hair follicle and intestinal epithelium are also affected by these agents. The present invention, by suppressing growth in at least some of these cells may protect them from the chemotherapy agents and thus allow for a more intense or longer period of chemotherapy treatment.

The preparations of the present invention may be used with a variety of chemotherapy agents. Some classes of agents include alkylating agents such as nitrogen mustards, ethylenimines and methylmelamines, alkyl sulfonates, nitrosoureas, triazenes and the like; antimetabolites such as folic acid analogs, pyrimidine analogs, in particular fluorouracil and cytosine arabinoside, and purine analogs and the like; natural products such as vinca alkaloids, epipodophyllotoxins, antibiotics, enzymes and biological response modifiers; and miscellaneous products such as platinum coordination complexes, anthracenedione, substituted urea such as hydroxyurea, methyl hydrazine derivatives, adrenocorticoid suppressants and the like. See for example, Goodman and Gilman's *The Pharmacological Basis of Therapeutics*, 8th edition, Pergamon Press, section XII, incorporated herein by reference.

The chemotherapy agents are administered orally, intravenously, intramuscularly, intrapleurally or intraperitoneally at doses based on the body weight and degree of disease progression of the patient, and may be given in one, two or even four daily administrations. Dosages range from about 0.5 mg/kg per day up to tens and even hundreds of mg/kg per day depending on the chemotherapy agent being administered and the patients weight and condition. The preparation of the present invention may be administered in conjunction with the chemotherapeutic agent. "In conjunction with" means that the pharmaceutical composition is administered either in a single composition or separately, either before, after or concurrently with the chemotherapy agent. Dosages of the myelosuppressive preparation will also depend on the body weight of the patient and on the amount of chemotherapy agent administered. Dosages will range from about 3 µg/kg per day to about 100 µg/kg per day, and may be administered intravenously, intramuscularly or intraperitoneally, for example. The exact dosage will be determined by the practitioner for each individual case.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Cloning of IP-10

The cloning of IP-10 cDNA and the affinity purification of antibodies against residues 10–98 (anti-IP-10), and 77–98 (anti-22) of IP-10 have been described elsewhere (Luster et al., 1985, Luster et al., 1987). Below is a brief description of the procedures.

Cell Culture

Human endothelial cells were isolated from umbilical cord veins (Jaffe et al., 1973) and grown in M199 medium supplemented with 20% heat-inactivated human serum, penicillin (100 U/ml), and streptomycin (100 µg/ml). All the studies were performed on second-passage human umbilical cord endothelial cells (HUVE). A primary keratinocyte cell line isolated from human foreskin was obtained from Clonetics Corporation (Boulder, Colo.) and maintained in a defined keratinocyte growth medium (Tsao et al., 1982). PBMC were isolated from venous blood fractionated on a Ficoll-Hypaque gradient. Monocytes were isolated from these PBMC by Percoll gradient fractionation (Wright and Silverman, 1982) and maintained in α-modified Eagle's medium (αMEM) supplemented with 10% heat-inactivated autologous human serum or fetal calf serum (FCS), penicillin, and streptomycin. FS4 cells were grown in αMEM supplemented with 10% FCS, penicillin, and streptomycin.

All induction experiments were performed in the regular cell growth media, using cells just before reaching confluence. Monocytes were induced at $10^6$ cells/ml in Teflon dishes.

IFN-γ

The IFN-γ was a highly purified recombinant protein synthesized in *E. coli* generously provided by Genentech, Inc., San Francisco, Calif. The endotoxin levels were determined in a limulus amoebocyte lysate assay before shipping. The human rIFN-γ had a specific activity of $2-4\times10^7$ U/mg as determined in a human lung carcinoma A549 inhibition assay using the encephalomyocarditis virus.

Peptide Synthesis

The peptide was synthesized by the solid-phase method (Barany and Merrifield, 1979) using chloromethylated, 1% crosslinked, styrene-divinylbenzene copolymer (Merrified Resin). Deprotection was followed by a coupling program that used the symmetric anhydrides of the appropriate Boc amino acids (Bachem Inc., Torrance, Calif.; or Peninsula Laboratories, Inc., Belmont, Calif.) (Yamashiro and Li, 1978). The side-chain functionalities were protected by benzyl-type protecting groups. The peptide was cleaved from the resin and deprotected by treatment with liquid HF-anisole at –0° C. (Scotchler et al., 1970). The peptide was purified by gel-permeation chromatography, ion-exchange chromatography, and reverse-phase HPLC. The final product was homogeneous by analytical reverse-phase HPLC.

The peptide was glutaraldehyde coupled to keyhole limpet hemocyanin (KLH) (Pfaff et al., 1982). 2 μg of peptide was dissolved 10 μl of $H_2O$ and added to 15 ng KLH in 2 ml 0.1M PBS. Glutaraldehyde (21 mM) was added over 1 h at room temperature. The mixture was allowed to stand overnight at room temperature and then was dialyzed against PBS.

Approximately 100 μg of protein in CFA was used to immunize two 8-wk-old female New Zealand white rabbits. The rabbits were boosted twice at 1-mo intervals with the same amount of protein in IFA. 10 d after the second boost, the rabbit was bled and serum was isolated and used for Western blotting and immunoprecipitation.

E. coli Expression and Production of Antiserum

A 576-bp Xba I-Eco RI insert derived from the IP-10 cDNA plasmid pIFNγ-31.7 (Matsuura, 1987) was cloned into the fusion expression vector pB4+ (Leammli, 1970). The pB4+ vector contains the gene for the influenza vital protein NSI. The plasmid was transformed into the E. coli strain AR58, which is a λ lysogen containing a temperature-sensitive mutation in the CI gene (CI857). The resulting strain, harboring the recombinant expression plasmid, produced a fusion protein at the nonpermissive temperature that consisted of 81 amino acids of NSI and 72 amino acids of IP-10.

A 325-bp Fnu4H fragment derived from the IP-10 cDNA plasmid pIFNγ 31.7 was cloned into the nonfusion expression vector pT17. This recombinant plasmid was transformed into the E. coli strain AR58, which upon temperature induction synthesized 88 amino acids of the IP-10 protein.

Bacterial cells were grown in L-broth at 30° C. to an $OD_{650}$ of 0.3, then shifted to 42° C. for 1 h of growth. The bacterial cells were pelleted by centrifugation and resuspended in 1/20 vol of PBS. The cells were lysed by sonication and subjected to centrifugation at 10,000 rpm for 5 min. The pellet, which included the recombinant proteins and cellular envelopes, was suspended in sample buffer and subjected to preparative SDS-PAGE. The gel was stained with Coomassie Brilliant Blue R for 1 min and immediately washed five times in deionized water. The faintly stained band was excised from the gel with a razor blade and minced. The gel pieces were soaked for 24 h in 50 mM Tris, pH 7.5, containing 0.15M NaCl and 0.1% SDS. The amount of eluted protein recovered was estimated by comparison to protein standards (Bio-Rad Laboratories, Richmond, Calif.) after SDS-PAGE. This treatment of the sample resulted in a preparation highly enriched for recombinant proteins.

Approximately 100 μg of protein in CFA was used to immunize an 8-wk-old female New Zealand white rabbit. The rabbit was boosted twice at 1-mo intervals with the same amount of protein in IFA. 10 d after the second boost, the rabbit was bled and serum was isolated and used for Western blotting and immunoprecipitation.

IgG was isolated from serum by protein A-Sepharose affinity chromatography (Pharmacia Fine Chemicals, Piscataway, N.J.). 1 mg of the gel-purified recombinant protein was coupled to cyanogen bromide-activated Sepharose 4B (Pharmacia Fine Chemicals). 100–200 mg IgG was affinity purified on the recombinant protein column. The bound IgG was eluted with 1M glycine-HCl, pH 2.8, quickly neutralized with 2M Tris, and dialyzed against PBS. The affinity-purified antiserum was used for immunoprecipitation, immunofluorescence, and immunohistochemistry.

Pulse-chase Experiments

HUVE cell monolayers (~$10^6$ cells) were washed twice with PBS and maintained for 30 min in αMEM lacking methionine but containing 200 mM glutamine. Cells were then pulsed for 30 min in this cell-starvation medium supplemented with [$^{35}S$]methionine (500 μCi/ml). After removal of the pulse medium, the cells were washed twice with PBS and then incubated with cell growth medium supplemented with unlabeled methionine (5 mM) for the chase periods indicated. At the completion of the chase, the monolayers were washed twice with PBS and scraped into an SDS solution (0.5% SDS, 50 mM Tris, pH 7.4, 100 mM NaCl, 2 mM EDTA). After being heated for 2 min at 100° C., the samples were frozen at –20° C. For immunoprecipitation, the samples were again heated for 2 min at 100° C., sonicated for 2 min, and adjusted to contain 0.2 U/ml aprotinin (Sigma Chemical Co., St. Louis, Mo.), and 1 mM PMSF (Sigma Chemical Co.). Affinity-purified antibodies were added to a final concentration of 5 μg/ml and the immunoprecipitation was continued as described below.

Immunoblotting

E. coli cells or human cell lysates were dissolved in sample buffer (2% SDS/0.0625M Tris, pH 7.4/10% glycerol/ 0.01% bromphenol blue/and 5% 2-ME), boiled for 5 min, and fractionated by SDS-PAGE using slab gels of 12.5 and 15% acrylamide. Prestained protein molecular weight standards (Bethesda Research Laboratories, Gaithersburg, Md.) were used to calculate apparent molecular weights. Protein was transferred electrophoretically to nitrocellulose (Schleicher & Schuell, Inc., Keene, N.H.). All of the following steps were performed in Tris-buffered saline (TBS; 50 mM Tris, pH 7.5, 2 mM EDTA, 0.15M NaCl), 0.5% NP-40, and 0% FCS. The nitrocellulose filter was first treated overnight in 5% nonfat dry milk, followed by incubation for 2 h with a 1:1,000 dilution of antiserum. The nitrocellulose was washed and reacted for 1 h with $10^6$ cpm/ml of $^{125}I$ Staphylococcus protein A (Amersham Corp., Amersham, Arlington Heights, Ill.). After extensive washing in TBS+0.5% NP-40, the filter was exposed to x-ray film at –70° C. in the presence of an intensifying screen.

Immunoprecipitation

Approximately $10^6$ cells were lysed in PBS containing 1% NP-40, 0.2 U/ml aprotinin, 1 mM PMSF, and 0.1% diisopropylfluorophosphate (Sigma Chemical Co.). Nuclei and debris were removed by centrifugation at 14,000 g for 5 min. The lysate was adjusted to 0.2% SDS and boiled for 5 min at 100° C. The lysate was further clarified by centrifugation at 45,000 g, 15 min at 4° C. The supernatant was passed through a 0.45-μm millex filter and further clarified by centrifugation at 45,000 g, 15 min at 4° C. Affinity-purified antibodies were added to a final concentration of 5 μg/ml to both lysate and supernatant. The solution was incubated at room temperature for 4-16 h. Antigen-antibody complexes were precipitated by incubation with protein A-Sepharose for 2 h at room temperature.

The immunoabsorbed protein A-Sepharose beads were collected by centrifugation, washed twice in buffer that contained 0.6M NaCl, 0.0125M $KPO_4$, pH 7.4, and 0.02% $NaN_3$ (HSA buffer), twice at room temperature with a mixed detergent solution (0.05% NP40, 0.1% SDS, 0.3M NaCl, and 10 mM Tris-HCl, pH 8.6), once again with HSA buffer, and finally, once in PBS. The antigen-antibody complexes were released from the beads by incubation at 100° C. for 2 min in 2× PAGE sample buffer.

$NH_2$-Terminal Sequence Determination

Human keratinocytes were biosynthetically labeled with [$^3$H]leucine and [$^{35}$S]cystein for 8 h. Radiolabeled IP-10 was purified from the keratinocyte media by immunoprecipitation and SDS-PAGE. The gels were dried down without fixing or staining. The IP-10 protein was located in the gel by autoradiography, electroeluted from the gel, and concentrated by precipitation (Schragger, 1987). Samples were subjected to automated Edman degradation in a Gas Phase Sequencer (Model 470A; Applied Biosystems, Inc., Foster City, Calif.). The amino acid derivative obtained at each cycle was dissolved in 20% acetonitrile and transferred to 10 ml of Aquasol for scintillation counting.

ELISA

The antipeptide antisera were checked for their ability to react with the synthetic peptide by an ELISA assay. Microtiter plates were coated with peptide (100 ng/well) in a sodium carbonate buffer, pH 9.6, and then saturated with 3% BSA. PBS, 0.1% Tween 20. One hundred microliters of antipeptide antisera dilutions from $10^{-2}$ to $10^{-7}$ were placed in the wells and incubated for 2 h. After extensive washing in PBS/0.05% Tween, the plates were incubated for 2 h with peroxidase-labeled affinity-purified goat anti-rabbit IgG. The wells were then washed and the substrate O-phenylenediamine (100 μl of 10 mg/25 ml in 0.05M citrate phosphate buffer, pH 5) was added. The reaction was allowed to proceed for 10 min at room temperature and was stopped by addition of 50 ml of 2.5M $H_2SO_4$. Absorbance was read at 410 nm in an automatic plate reader (Minireader II; Dynatech Laboratories, Inc., Alexandria, Va.). Positive ELISA readings were obtained at dilutions of $10^{-7}$ after boosting with peptide conjugate. The purified peptide was attached to CNBr-activated Sepharose 4B. This matrix was used to affinity purify the rabbit antipeptide antiserum. The affinity-purified antibodies were used for Western blotting and immunoprecipitation experiments.

RNA Isolation and Blotting

Total cellular RNA was isolated by the guanidinium isothiocyanate-cesium chloride method. RNA was fractionated on a 1% agarose gel containing 2.2M formaldehyde (Irie, 1980) and transferred to nitrocellulose (Michaels, 1991) and hybridized with a random primed (Towbin, 1979) IP-10 cDNA probe (pIFNγ-31.7). Hybridization was performed at 40° C. for 16 h in a solution containing 50% formamide, 10% dextran sulfate, 5× SSC (1× SSC: 0.15M sodium chloride, 0.015M sodium citrate), 1× Denhardt's (0.02% polyvinyl-pyrrolidone, 0.02% Ficoll, and 0.02% BSA), and 200 μg/ml of sonicated herring sperm DNA. The filters were washed at 50° C. in 0.1× SSC containing 0.1% SDS and exposed at −70° C. to Kodak XAR film in the presence of one intensifying screen (Cronex Lightning Plus).

EXPRESSION OF RECOMBINANT IP-10

Recombinant IP-10 has been expressed in both insect and bacterial systems as described in Examples II and III. The IP-10 secreted from insect cells appears to be lacking the signal sequence, which is also removed from the naturally occuring protein which is secreted from keratinocytes, for example. In addition, the full length protein and two smaller fragments have been produced by a bacterial expression system.

EXAMPLE II

Expression in Insect Cells

Materials and Methods

All chemicals were reagent grade. Protein molecular weight markers were from BRL (Gaithersburg, Md.). Ficoll-Hypaque, Protein A-Sepharose, and S-Sepharose were from Pharmacia (Piscataway, N.J.). EX-CELL-400 was from JR Scientific (Woodland, Calif.). The 4.6×150 mm C4 reverse phase column was from Vydac (Hesperia, Calif.). The Rapid-Ag Silver protein staining kit was from ICN (Cleveland, Ohio).

Wild type baculovirus, Sf9 insect cells, and transfer vector pVL1392 (Webb and Summers, 1990) were provided by M D Summers (Texas A&M University, College Station, Tex.). Transfer vector pAcYM1 (Matsuura et. al., 1987) was provided by D. Bishop (NERC Institute of Virology, Oxford, UK). The Pst-1 fragment of the IP-10 cDNA was cloned in the Pst-1 site of pVL1392, and yielded recombinant baculoviruses 8555 and 9094. For elimination of its 5' untranslated sequences, the IP-10 cDNA was digested with Nla3, the 375 nucleotide fragment was purified, ligated to GATCCATG, restricted with BamH1, and cloned into the BamH1 site of pAcYM1, generating recombinant baculoviruses A213 and A221. Standard techniques were performed for isolation of recombinant baculoviruses (Webb and Summers, 1990; Sambrook et. al., 1989). All junctions between recombinant transfer vectors and IP-10 cDNA were sequenced (Sanger et. al., 1987) to exclude cloning artifacts. For production of rIP-10, Sf9 cells were infected with A221 (20 PFU/cell), 6-day supernatants were cleared at 100,000 G for 1 h at 4° C., dialyzed against 40 mM Na Phosphate pH 7.2, and loaded on a 15 ml Sepharose-S FPLC column. Proteins were eluted with a linear gradient of 0.0–2.0M NaCl in 40 mM Na Phosphate pH 7.2 (150 ml), fractions containing rIP-10 were identified with a dot blot immunoassay (Sarris et. al., 1992) using anti-IP-10, and were loaded on a reverse-phase C4 HPLC column. Adsorbed rIP-10 was eluted with a gradient of 25% acetonitrile-50% propanol-25% $H_2O$ in 0.1% TFA, lyophilized and resuspended in endotoxin-free PBS.

Proteins were separated on 10–20% gradient PAGE in the presence of 0.1% SDS with 0.75M Tris-HCl, pH 8.45, in the stacking gel; 1.0M Tris-HCl, pH 8.45, in the separating gel; 0.2M Tris HCl, pH 8.9 in the anode reservoir; and 0.1M Tris-0.1M Tricine in the cathode reservoir (Schrägger and von Jagow, 1987). Protein gels were stained with silver (Irie, 1980), and quantitated by densitometry. Western blots were performed on Immobilon-P (Sarris et. al., 1992; Towbin et. al., 1979). rIP-10 was immunoprecipitated from Sf9 cells labeled with [$^{35}$S]-methionine after boiling in 500 μl of 0.2% SDS, 50mM Tris-HCl, pH 7.5, and the sequential addition of NP-40 (final concentration of 1%), affinity purified antibodies (final concentration 5 μg/ml), and Protein-A beads (Sarris and Palade, 1982). The $M_r$ of IP-10 was estimated from the mobilities of marker proteins of 43–14.3 kDa. Amino-terminal sequencing was performed as described (Hewick et. al., 1981; Tempst and Riviere, 1989).

19

Results

Recombinant baculoviruses 8555, 9094, A213 and A221 express rIP-10 as a nonfusion protein. In baculovirus 8555 the initiating codon, ATG of the polyhedrin gene is mutated to ATT, and protein synthesis starts 118 nucleotides downstream, at the initiating ATG of the IP-10 cDNA. In baculovirus 9094 the IP-10 was inserted in the same location but in reverse orientation. In A221 and A213 the initiating ATG of the polyhedrin gene is destroyed by deletion of nucleotides 2–751 of its coding region, and protein synthesis starts 8 nucleotides downstream at the initiating ATG of IP-10. Most 3'-untranslated sequences of the IP-10 were deleted from A213 and A221.

Analysis of protein synthesis after infection by 8555 and A221 demonstrated a major new band of 9.9 kDa, similar in size to IP-10 without the signal sequence (10.0 kDa), and a minor band of 11.9 kDa, similar in size to IP-10 with the signal sequence (12.4 kDa). Neither band was detected in uninfected cells or in cells infected with 9094 or with wild type virus (FIG. 1A). The 9.9 kDa but not the 11.9 kDa band was detected in supernatants of infected cells by autoradiography. Non-immune serum did not precipitate any proteins from cells infected with A221, but anti-IP-10 and anti-22 precipitated both bands (FIG. 1B). Western blotting with anti-IP-10 and anti-22 detected both bands in cells, but only the 10 kDa band in the media.

Figures 2A, 2B:
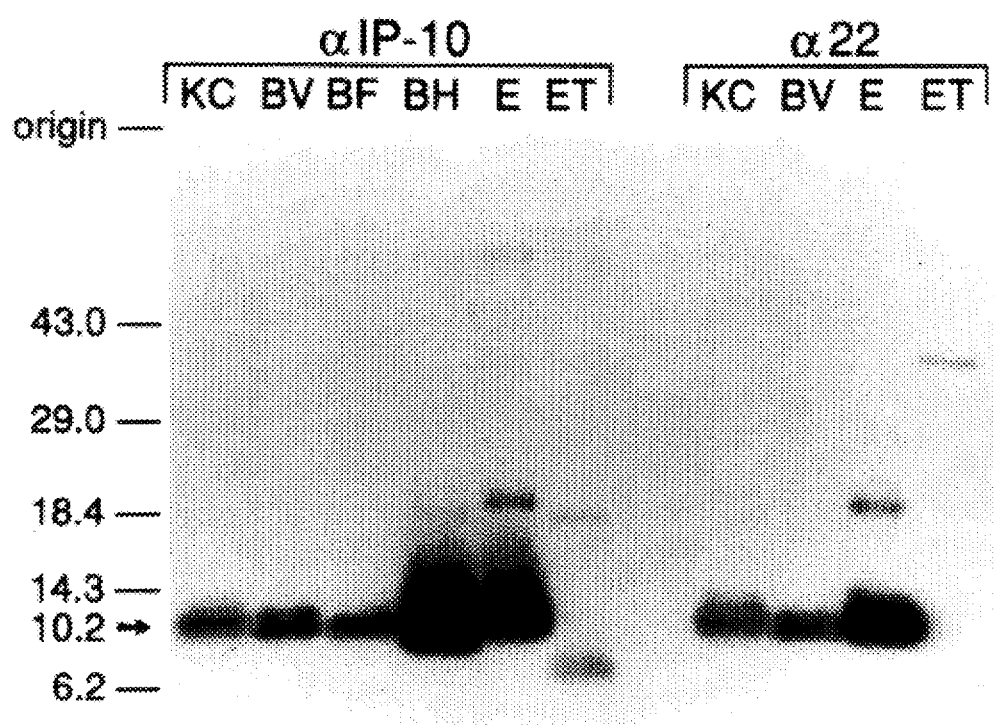
FIGS. 2A and 2B. Western blot analysis of natural and rIP-10. Keratinocyte IP-10 (KC), supernatants from A221-infected Sf9 cells (BV), and representative fractions from Sepharose-S FPLC (BF) or C4 reverse phase HPLC (BE) were analyzed by SDS-PAGE along with f(22–98) (E) or f(22–77) (ET).

In order to precisely define the $M_r$ of baculovirus IP-10, f(22–98) and f(22–77) were used as molecular weight markers. These studies demonstrated that f(22–98) and IP-10 derived from either keratinocytes or baculovirus co-migrated at 10.2 kDa, and were recognized by anti-IP-10 and anti-22. Alternatively, f(22–77) migrated with an apparent $M_r$ of 6.2 kDa, and was recognized by anti-IP-10 but not by anti-22 (FIG. 2). The reactions of antiserum AS522 and anti-IP-10 in immunoprecipitations and western blots were identical.

Figure 3A:
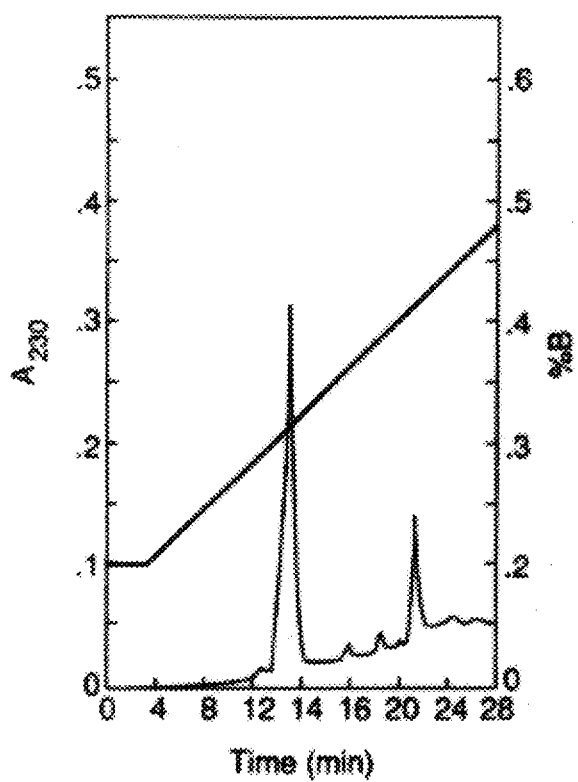
FIGS. 3A and 3B. Purification of rIP-10 from baculovirus-infected cells.
Figure 3B:
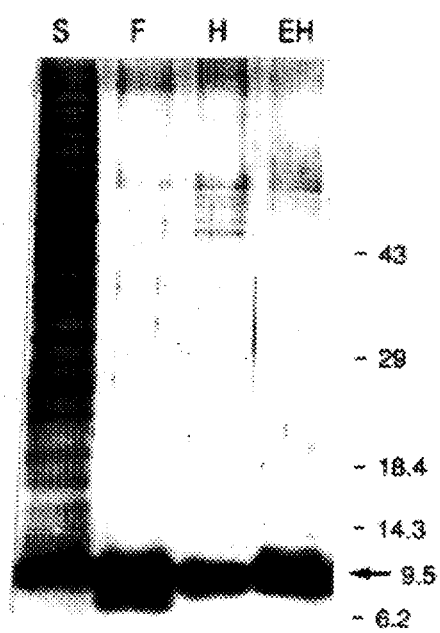

Levels of rIP-10 were 5–10 times higher after infection with A213 and A221 than after infection with 8555, and were not affected by FCS reaching 9% of the total protein in the supernatant of cells grown in EXCELL-400. Anti-IP-10 and a dot blot immunoassay were used to purify rIP-10 from supernatants of infected cells, and a major HPLC peak was obtained (FIG. 3A) which was a single band on SDS-PAGE (FIG. 3B, lanes S, F, H) co-migrating with purified bacterial f(22–98) (FIG. 3B, lane E). The faint bands near the top of the gels correspond in size to keratins, and were seen in unloaded lanes and in lanes loaded only with sample buffer. Western blotting confirmed that the purified band represented rIP-10, because it reacted with anti-IP-10 and anti-22 during all stages of purification (FIG. 2).

Aminoterminal sequencing of baculovirus rIP-10 demonstrated a major amino terminal sequence of VPLSRTVRØT SEQ ID NO:4 (66%) and a minor sequence of RTVRØT SEQ ID NO:5 (34%), both matching the sequence of IP-10 secreted by keratinocytes (Luster et al., 1987). The purified baculovirus IP-10 thus appears to be identical to natural IP-10. The amino acid sequence of the major species is V P L S R T V R C T C I S I S N Q P V N P R S L E K - LEIIPASQFCPRVEIIATMKKKGEKRCLNPESKAIKNLL KAVSKEMSKRSP (residues 2–78 SEQ ID NO:6, i.e. lacking the N-terminal Methionine). The yield of purified rIP-10 was 0.5 µg/ml of supernatant in the baculovirus system.

EXAMPLE III

Expression in Bacterial Cells

This section describes the generation and purification of two forms of recombinant IP-10; f(22–98) which is identical to the naturally occurring IP-10 but has an added methionine at its amino terminal, and f(22–77) which differs from f(22–98) by a deletion of the last 21-carboxy-terminal amino acids.

Using two primers, A (GGATCCATGGTACCTCTCTCTAGAACC; seq id no:1) as 5' and B (GGATCCATGGTTAAGGAGATCTTTTAGA; seq id no:2) as 3' primer, a cDNA coding for f(22–98) was amplified (Saiki et. al., 1988). This segment, f(22–98) is a fragment lacking the signal peptide and extending from valine 22 to proline 98 of IP-10. With C (GGATCCATGGTTATGGATTCAGACATCTCTT; seq id no:3) as 3' and A as the 5' primer a cDNA coding for f(22–77) was also amplified. This segment encodes a fragment extending from valine 22 to proline 77 and lacking the signal peptide and the last 21 residues of IP-10, but retaining all 4 cysteine residues and approximating the previously reported, secreted form of IP-10 (Luster et al., 1987). The PCR products were restriction digested with Nco1 and cloned in the Nco1 site of pET-3d (provided by F. Studier, Brookhaven National Laboratories, New York) eliminating all amino acid residues of φ10 (Studier et. al., 1990), and expressing the rIP-10 fragments as nonfusion proteins with an added methionine at the amino terminus. The regions adjacent to and including the IP-10 cDNA were sequenced (Sanger et al., 1987) to exclude PCR and cloning errors. Lysogens BL21(DE3) transformed with recombinant plasmids were induced with 0.4 mM isopropylthiogalactoside (Studier et al., 1990), recombinant f(22–98) was purified (Lindley et al., 1988) from refractile bodies (Marston), dialysed against Ca/Mg-free PBS, and stored in 1 ml aliquots at −70° C. Protein concentration was measured by dye binding (Bradford, 1976).

Sequencing of f(22–98) demonstrated a single amino-terminal sequence of MVPLSRTVROTOISISNQPVN SEQ ID NO:7 matching the sequence of secreted IP-10 (Luster et al., 1987) with an additional amino-terminal methionine. The yield of bacterial IP-10 [f(22–98)] was 5 µg/ml of bacterial culture. The sequences of bacterial IP-10 were: f(22–98)

| | |
|---|---|
| MVPLSRTVRCTCISISNQPVNPRSLEKLEIIPASQFCPRVEIIATMKKKGEKRCLNPESKAIKNLLKAVSKEMSKRSP | (SEQ ID NO: 8); and f(22–77) |
| MVPLSRTVRCTCISISNQPVNPRSLEKLEIIPASQFCPRVEIIATMKKKGEKRCLNP | (residues 1–57 of SEQ ID NO: 9). |

EXAMPLE IV

Colony Suppression by IP-10

Material and Methods rIFN-γ was a gift from Dr G. Garotta (Hoffman-LaRoche, Basel Switzerland). Human rMIP-1α and rMIP-2α were gifts of Dr B. Sherry (Picower Institute, Manhasset, N.Y.). Human rGM-CSF, human rIL-3 and human rSLF were gifts of the Immunex Corporation (Seattle, Wash.). Human rEPO was purchased from Amgen (Thousand Oaks, Calif.), human platelet Factor 4 (PF4) and rIL-8 from Sigma (St Louis, Mo.), and human rMCAF from ReproTech Inc, Rocky Hills, N.J.

Human bone marrow CFU-GM, BFU-E, and CFU-GEMM of healthy volunteers were assayed as described (Broxmeyer et al., 1990; Broxmeyer et. al., 1991; Broxmeyer et. al., 1993). rSLF (50 ng/ml) and other recombinant or natural chemokines were added as indicated. Highly purified CD-34$^{+++}$ cells (Broxmeyer et al., 1990; Broxmeyer et. al., 1993) were plated (500 cell/ml) in the presence of rEPO (1 U/ml), rSLF (50 ng/ml), rGM-CSF (100 U/ml) and rIL-3 (200 U/ml), and yielded 126±10, 60±10 and 17±5 CFU-GM, BFU-E and CFU-GEMM per 500 plated cells, respectively. For reversal of inhibition, chemokines were pre-incubated with a 4-fold molar excess of affinity purified antibodies (anti-IP-10 or anti-22) or with whole serum (AS522) in McCoy's media at room temperature for 1 h. The mixture was added to human bone marrow cells and CFU-GM were assayed in McCoy's media supplemented with FCS, rSLF (50 ng/ml) and GM-CSF (100 U/ml). For controls, an equal volume of similarly incubated McCoy's medium was added to cells. Statistical significance was determined with the Student's two-tailed test.

Results

Figure 4A:
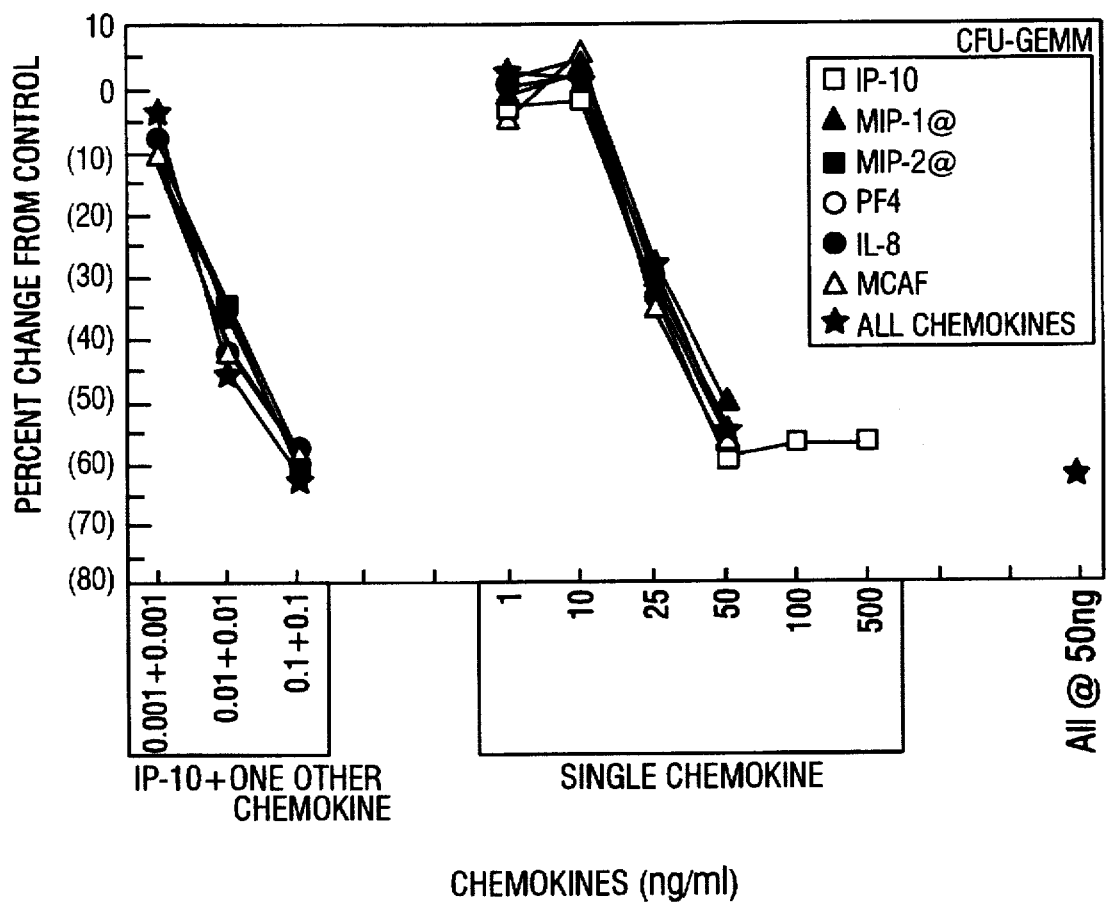
FIGS. 4A, 4B and 4C. Influence of rIP-10 on colony formation. CFU-GM were plated in the presence of rGM-CSF (100 U/ml) and rSLF (50 ng/ml). CFU-GEMM and BFU-E were plated in the presence of rEPO (1 U/ml) and rSLF (50 ng/ml). Results are given as the mean±SEM and reflect 3 separate experiments with rIP-10, and 2–3 experiments for the other chemokines. Percent changes from control designate suppression and were based on control colony numbers for CFU-GM (59±2 to 106±7), BFU-E (58±4 to 105±2), and CFU-GEMM (37±3 to 68±1). Most symbols in the graphs are smaller than the SEM, which was always ≦12% of the mean percent change.
Figure 4B:
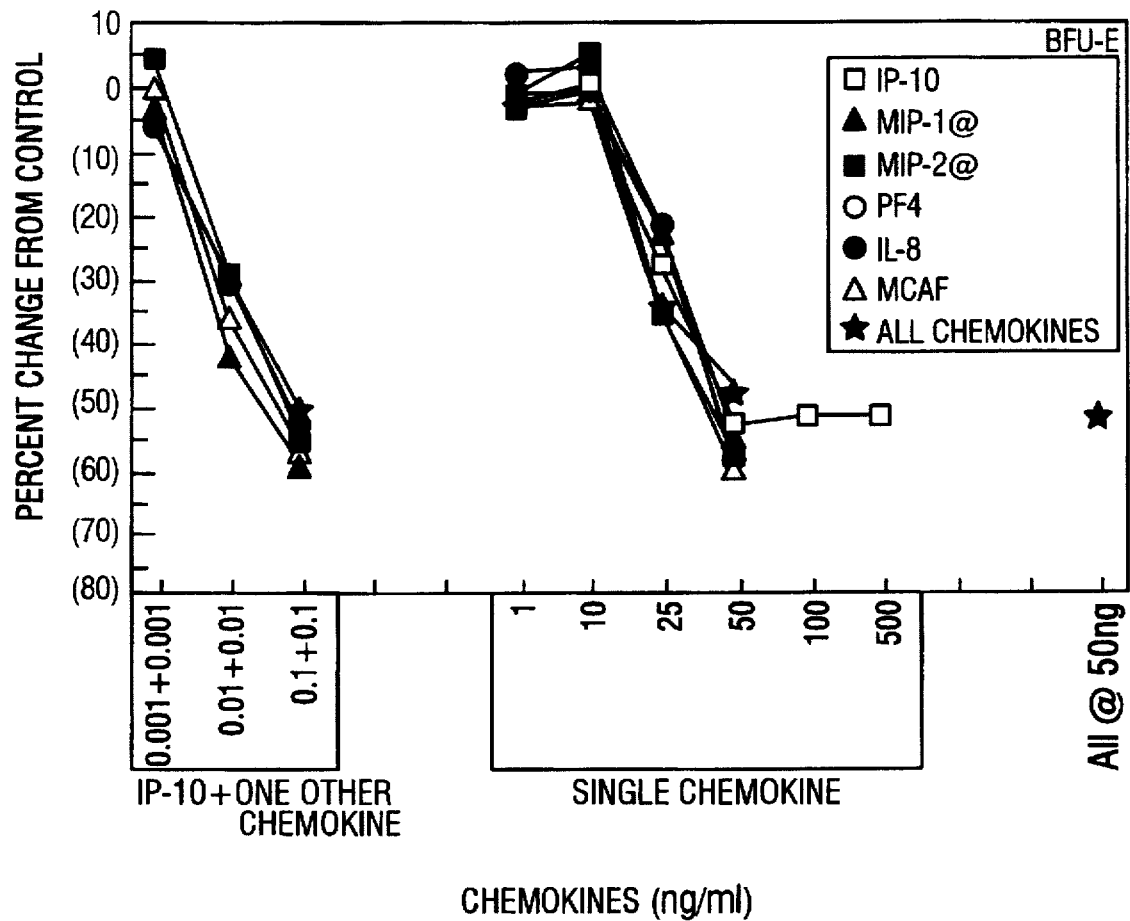
Figure 4C:
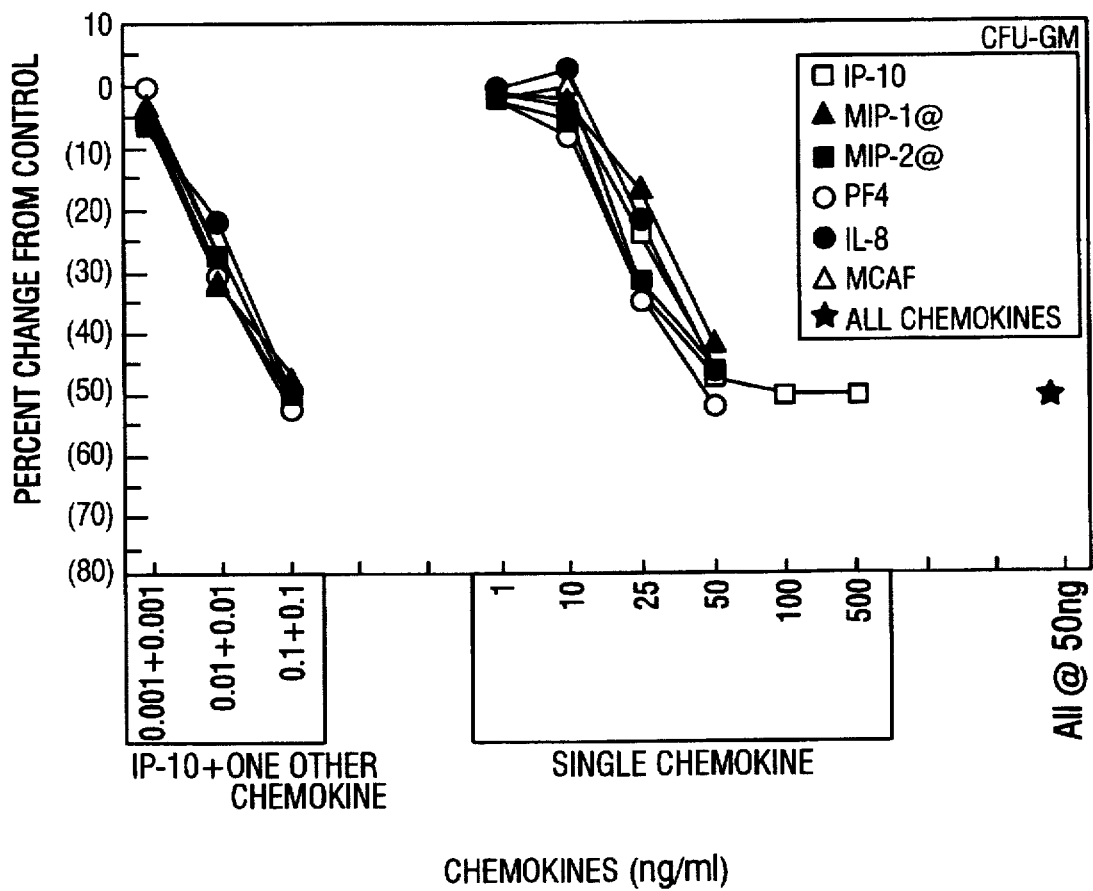

The effect of rIP-10 on colony formation by CFU-GM, BFU-E and CFU-GEMM was evaluated. rIP-10 (50 and 500 ng/ml) did not affect colony formation by marrow cells plated in media alone or in the presence of single growth factors (rEPO or rGM-CSF). However, rIP-10 suppressed colony formation of CFU-GM stimulated by rGM-CSF and rSLF, and BFU-E and CFU-GEMM stimulated by rEPO and rSLF. Concentrations of 1–10 ng/ml were inactive, but there was a dose dependent inhibition between 25 and 50 ng/ml. Maximal inhibition (50–60%) was seen at 50–500 ng/ml of rIP-10 (FIG. 4), representing complete suppression of the additional CFU-GM and BFU-E or CFU-GEMM colonies generated by-the respective addition of rSLF to rGM-CSF or rEPO. The dose response was similar to that of rMIP-1α, rMIP-2α, PF4, rIL-8, or rMCAF (Broxmeyer et. al., 1991; Broxmeyer et. al., 1993) which were assessed in the same assays. Whereas individual chemokines were inactive at concentrations <10 ng/ml, significant suppression of colony formation (p<0.01) was seen when 0.01 ng/ml of rIP-10 was combined with 0.01 ng/ml of rMIP-1α, rMIP-2α, PF4, rIL-8, or rMCAF. Combinations of 0.1 ng/ml of rIP-10 with 0.1 ng/ml of any of these chemokines resulted in a 50–60% inhibition of colony formation by CFU-GM, BFU-E and CFU-GEMM (p<0.001). This represented complete inhibition of the rSLF-dependent colonies, and could not be suppressed further with combination of 50 ng/ml of rIP-10, rMIP-1α, rMIP-2, PF4, rIL-8, and rMCAF (FIG. 4). In the presence of rIP-10 (100 ng/ml) colony formation by CD-34$^+$++ cells was inhibited by 77% for CFU-GM (p <0.01), by 58% for BFU-E (p<0.05), and by 82% for CFU-GEMM (p<0.05).

The inhibitory activity of rIP-10 but not that of rMIP-1α or PF4 was neutralized by antibodies raised against whole IP-10 (anti-IP-10 and AS522). Antisera raised against the 22 carboxy-terminal residues of IP-10 (anti-22) did not affect the inhibitory activity of rIP-10, rMIP-1α, or PF4. These antibodies had no effect on colonies grown in the absence of rIP-10 (Table 1).

TABLE 1

Antibody against IP-10 neutralizes its ability to suppress CFU-GM in vitro. Colony Formation after Preincubation with:

|  | media | anti-IP-10 | AS522 | anti-22 |
|---|---|---|---|---|
| Chemokine media | 61 ± 1 | 64 ± 1 (+2) | 61 ± 1 (0) | 63 ± 2 (+3) |
| IP-10 | 34 ± 3(−44)* | 62 ± 1(+2) | 61 ± 2(0) | 32 ± 2 (−48)* |
| MIP-1α | 33 ± 2 (−46)* | 32 ± 3 (−48)* | 37 ± 2 (−39)* | 33 ± 2 (−46)* |
| PF4 | 31 ± 1 (−49)* | 34 ± 2 (−44)* | 36 ± 1 (−41)* | 33 ± 2 (−48)* |

CFU-GM grown with GM-CSF (100 U/ml) and SLF (50 ng/ml) are expressed as mean ± 1 SEM per 10$^5$ plated cells.
Chemokines were used at 50 ng/ml.
Purified f(22-98) was the source of rIP-10.
Values in parentheses designate percent inhibition relative to control.
*designates significant decrease (p < 0.001) relative to control.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Barany, G. and R. B. Merrifield. 1979. Solid phase peptide synthesis. In The Peptides. Vol. II. E. Gross and J. Meinhoper, editors. Academic Press, New York. 1–284.

Bradford M. 1976. A rapid and sensitive method for the quantitation of microgram quantities of protein utilizing the principle of protein-dye binding. Anal Biochem, 72:248.

Broxmeyer, H. E, B Sherry, S. Cooper, L. Lu, R. Maze, M. P. Beckmann, A. Cerami and P. Ralph. 1993. Comparative analysis of the human macrophage inflammatory protein family of cytokines (chemokines) on proliferation of human myeloid progenitor cells: interacting effects involving suppression, synergistic suppression and blocking of suppression. J Immunol, 150:3448.

Broxmeyer, H. E., B. Sherry, S. Cooper, F. W. Ruscetti, D. E. Williams, P. Arosio, B. S. Kwon, and A. Cerami. 1991. Macrophage inflammatory protein (MIP)-1b abrogates the capacity of MIP-1α to suppress myeloid progenitor cell growth. J Immunol., 147:2586.

Broxmeyer, H. E., B. Sherry, L. Lu, S. Cooper, K.-O. Oh, P. Tekamp-Olson, B. S. Kwon, and A. Cerami. 1990. Enhancing and suppressing effects of recombinant murine macrophage inflammatory proteins on colony formation in vitro by bone marrow myeloid progenitor cells. Blood, 76:1110.

Chirgwin, J. M., A. E. Przybyla, R. J. MacDonald, and W. J. Rutter. 1979. Isolation of biologically active ribonucleic acid from sources enriched in ribonuclease. Biochemistry. 18:5294.

Dimitriadis, G. J. 1979. Effect of detergents on antibody-antigen interaction. *Anal Biochem*, 98:445.

Dunlop, D. J., E. G. Wright, S Lorimore, G. J. Graham, T. Holyoake, D. J. Kerr, S. D. Wolpe, and I. B. Pragnell. 1992. Demonstration of stem cell inhibition and myeloprotective effects SCI/rhMIP1a in vivo. *Blood*, 79:2221.

Feinberg, A. P., and B. Vogelstein. 1983. A technique for radiolabeling DNA restriction endonuclease fragments to high specific activity. *Anal. Biochem.* 132:6.

Graham, G. J., E. G. Wright, R. Rewick, S. D. Wolpe, N. M. Wilkie, D. Donaldson, S. Larimore, and I. B. Pragnell. 1990. Identification and characterization of an inhibitor of hematopoietic stem cell proliferation. *Nature*, 344:442.

Hewick, R. M., M. W. Hunkapiller, L. E. Hood, and W. J. Dreyer. 1981. A gas-liquid solid phase peptide and protein sequenator. *J Biol Chem*, 256:7990.

Irie, S. 1980. A highly sensitive silver staining for detection of proteins in polyacrylamide gels. *Biochemistry* (Japan), 52:411.

Jaffe, E. A., R. C. Nachman, C. G. Becker, and C. R. Minick. 1973. Culture of human endothelial cells derived from umbilical veins. Identification by morphologic and immunologic criteria. *J. Clin. Invest.* 52:2745.

Kahn, J., Ruiz, R., Kerschmann, R., Berger, T., Ma, R., Coleman, R., Alford, B. and L. Kaplan. 1993. A phase ½ study of recombinant platelet factor 4 (rPF4) in patients with AIDS related Karposi's Sarcoma, *Proc Amer Soc Clin Oncology* 12:4a.

Lehrach, H., D. Diamond, J. M. Worney, and H. Boedtler. 1977. RNA molecular weight determinations by gel electrophoresis under denaturing conditions, a critical reexamination. *Biochemistry.* 16:7443.

Lindley, I., H. Aschauer, J. M. Seifert, C. Lam, W. Brunowsky, E. Kownatzki, M. Thelen, P. Peveri, B. Dewald, V. von Tscharner, A. Waltz, and M. Baggiolini. 1988. Synthesis and expression in *Escherichia coli* of the gene encoding monocyte-derived neutrophil-activating factor: Biological equivalence between natural and recombinant neutrophil-activating factor. *Proc Natl Acad Sci USA*, 85:9199.

Lord, B. I., T. M. Dexter, J. M. Clements, M. A. Hunter and A. J. H. Gearing. 1992. Macrophage inflammatory protein protects multipotent hematopoietic cells from the cytotoxic effects of hydroxyurea in vivo. *Blood*, 79:2605.

Luster, A. D., and J. V. Ravetch. 1987. Biochemical characterization of a g Interferon-inducible cytokine (IP-10). *J Exp Med*, 166:1084.

Luster, A. D., J. C. Unkeless, and J. V. Ravetch. 1985. g-Interferon transcriptionally regulates an early-response gene containing homology to platelet proteins. *Nature*, 315:672.

Marston, F. A. O. The purification of eukaryotic polypeptides expressed in *Escherichia coli*. In "DNA Cloning: A Practical Approach" (Ed M Glover) vol 3, pp59, IRL Press, Oxford.

Matsuura, Y., R. D. Possee, H. A. Overton, and D. H. Bishop. 1987. Baculovirus expression vectors: the requirements for high level expression of proteins, including glycoproteins. *J Gen Virol*, 68:1233.

Maze, R., B. Sherry, B. S. Kwon, A. Cerami, and H. E. Broxmeyer. 1992. Myelosuppressive effects in vivo of purified recombinant murine macrophage inflammatory protein-1a. *J. Immunol*, 149:1004.

Oppenheim, J. J., C. O. C. Zachariae, N. Mukaida, and K. Matsushima. 1991. Properties of the novel proinflammatory supergene "intercrine" cytokine family. *Ann Rev Immunol.* 9:61.

Pfaff, E. P., M. Mossgay, H. B. Bohm, G. E. Schulz, and H. Schuller. 1982. Antibodies against a preselected peptide recognize and neutralize foot and mouth disease virus. *EMBO (Eur. Mol. Biol. Organ.) J.* 1:869.

Saiki, R. K., D. H. Gelfand, S. Stoffel, S. J. Scharf, R. Higuchi, G. T. Horn, K. B. Mullis, and H. A. Elrich. 1988. Primer-directed enzymatic amplification of DNA with a thermostable DNA polymerase. *Science*, 239:487.

Sambrook, J., E. F. Fritsch, and T. Maniatis. 1989. *Molecular cloning: A laboratory manual. Second edition.* Cold Spring Harbor Laboratory Press.

Sanger, F., S. Nickelson, and A. R. Coulson. 1977. DNA sequencing with chain-terminating inhibitors. *Proc Natl Acad Sci USA*, 74:5463.

Sarris, A. H., M. W. Harding, T. R. Jiang, D. Aftab, and R. E. Handschumacher. 1992. Immunofluorescent localization and immunochemical determination of Cyclophilin-A with specific rabbit antisera. *Transplantation*, 54:904.

Sarris, A. H., and G. E Palade. 1982. Immunofluorescent detection of erythrocyte sialoglycoprotein antigens on murine erythroid cells. *J Cell Biol.* 93:591.

Schrägger, H., and G. von Jagow. 1987. Tricine-sodium dodecyl sulfate polyacrylamide gel electrophoresis for the separation of proteins in the range from 1 to 100 kDa. *Anal Biochem*, 166:368.

Scotchler, J., R. Lozier, and A. B. Robinson. 1970. Cleavage of single amino acid residues from purified resin with hydrogen chloride and hydrogen fluoride. *J. Org. Chem.* 35:3151.

Shatzman, A., Y-S. Ho, and M. Rosenberg. 1983. Use of phage lambda regulatory signals to obtain efficient expression of genes in *E. coli*. In Experimental Manipulation of Gene Expression. Academic Press, New York. 1–14.

Shields, D., and G. Blobel. 1977. Cell free synthesis of fish preproinsulin, and processing by heterologous mammalian microsomal membranes. *Proc. Natl. Acad. Sci. USA.* 74:2059.

Southern, E. M. 1975. Detection of specific sequences among DNA fragments separated by gel electrophoresis. *J. Mol. Biol.* 98:503

Studier, F. W., A. H. Rosenberg, J. J. Dunn, and J. W. Dubendorff. 1990. Use of T7 polymerase to direct expression of cloned genes. *Methods in Enzymology*, 185:60.

Tempst, P., and L. Riviere. 1989. Examination of automated polypeptide sequencing using standard phenyl isothiocyanate reagent and subpicomole high-performance liquid chromatographic analysis. *Anal Biochem*, 183:290.

Tsao, M. C., B. J. Walthall, and R. C. Ham. 1982. Clonal growth of normal human epidermal keratinocytes in a defined medium. *J. Cell. Physiol.* 110:219.

Towbin, H., T. Staehelin, and J. Gordon. 1979. Electrophoretic transfer of proteins from polyacrylamide gels to nitro-cellulose sheets: Procedure and some applications. *Proc Natl Acad Sci USA*, 76:4350.

Webb, N. R. and M. D. Summers. 1990. Expression of proteins using recombinant baculoviruses. *Technique*, 2:173.

Wolpe, S. D., and A. Cerami. 1989. Macrophage inflammatory proteins 1 and 2: members of a novel superfamily of cytokines. *FASEB J*, 3:2565.

Wright, S. D., and S. C. Silverstein. 1982. Tumor-promoting phorbol esters stimulate C3b and C3b' receptor-mediated phagocytosis in cultured human monocytes. *J. Exp. Med.* 156:1149.

Yamashiro, D., and C. H. Li. 1978. Total synthesis of ovine β lipotropin by the solid-phase method. *J. Am. Chem. Soc.* 100:5174.

What is claimed is:

1. A method for inhibiting the growth of hematopoietic progenitor cells comprising contacting a population of cells that include hematopoietic progenitor cells with an effective amount of IP-10.

2. The method of claim 1, wherein the IP-10 comprises recombinant IP-10.

3. The method of claim 2, wherein the recombinant IP-10 comprises f(22–98) IP-10.

4. The method of claim 1, wherein IP-10 is prepared by a process that includes:

(a) preparing a recombinant host cell comprising a recombinant gene segment encoding IP-10;

(b) culturing said cell under conditions effective to allow expression of said gene to produce IP-10; and (c) collecting and purifying the IP-10 so produced.

5. The method of claim 1, wherein the IP-10 is comprised in a pharmaceutical composition.

6. The method of claim 5, wherein the pharmaceutical composition is administered to a human cancer patient.

7. The method of claim 6, wherein a therapeutically effective amount of an antineoplastic agent having bone marrow toxicity is administered to the patient, in conjunction with administration of the IP-10 pharmaceutical composition.

8. An improved method for chemotherapy of a cancer patient employing an antineoplastic agent having bone marrow toxicity, wherein the improvement comprises treating said patient with a hematopoietic progenitor cell inhibitory amount of IP-10.

9. A method for inhibiting the growth of hematopoietic progenitor cells in a patient comprising the steps of:

(a) preparing a recombinant host cell comprising a recombinant gene segment encoding IP-10;

(b) culturing said cell under conditions effective to allow expression of said gene to produce IP-10;

(c) collecting and purifying the recombinant IP-10 so produced;

(d) rendering said recombinant IP-10 pharmacologically acceptable; and (e) administering said pharmacologically acceptable IP-10 to said patient in an amount effective to inhibit hematopoietic progenitor cells.

10. The method of claim 9, wherein the IP-10 is produced from a baculovirus expression vector.

11. The method of claim 9, wherein the patient is a human cancer patient.

12. The method of claim 9, wherein the patient is administered an agent having bone marrow toxicity.

13. The method of claim 12, wherein the patient is a cancer patient, and the cancer patient is administered an antineoplastic agent having bone marrow toxicity.

14. The method of claim 9, wherein the recombinant gene segment encodes f(22–98) IP-10.

15. The method of claim 9, wherein the recombinant gene segment encodes full length IP-10.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i x ) SEQUENCE DESCRIPTION: SEQ ID NO:1:
        GGATCCATGG TACCTCTCTC TAGAACC ( 2 ) INFORMATION FOR SEQ ID NO:2:

( i ) SEQUENCE CHARACTERISTICS:
        ( A ) LENGTH: 28 base pairs
        ( B ) TYPE: nucleic acids
        ( C ) STRANDEDNESS: single
        ( D ) TOPOLOGY: linear ( i x ) SEQUENCE DESCRIPTION: SEQ ID NO:2:

GGATCCATGG TTAAGGAGAT CTTTTAGA                                      2 8

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i x ) SEQUENCE DESCRIPTION: SEQ ID NO:3:

GGATCCATGG TTATGGATTC AGACATCTCT T                            3 1

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: linear ( i x ) SEQUENCE DESCRIPTION: SEQ ID NO:4:

Val Pro Leu Ser Arg Thr Val Arg Xaa Thr
 1                5                      1 0

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i x ) SEQUENCE DESCRIPTION: SEQ ID NO:5:

Arg Thr Val Arg Xaa Thr
 1                5

( 2 ) INFORMATION FOR SEQ ID NO:6:

( i ) SEQUENCE CHARACTERISTICS:
        ( A ) LENGTH: 77 amino acid residues
        ( B ) TYPE: amino acids
        ( C ) STRANDEDNESS: single
        ( D ) TOPOLOGY: linear ( i x ) SEQUENCE DESCRIPTION: SEQ ID NO:6:

```
Val  Pro  Leu  Ser  Arg  Thr  Val  Arg  Cys  Thr  Cys  Ile  Ser  Ile  Ser  Asn
 1              5                   10                       15

Gln  Pro  Val  Asn  Pro  Arg  Ser  Leu  Glu  Lys  Leu  Glu  Ile  Ile  Pro  Ala
              20                   25                       30

Ser  Gln  Phe  Cys  Pro  Arg  Val  Glu  Ile  Ile  Ala  Thr  Met  Lys  Lys  Lys
              35                   40                       45

Gly  Glu  Lys  Arg  Cys  Leu  Asn  Pro  Glu  Ser  Lys  Ala  Ile  Lys  Asn  Leu
         50                        55                  60

Leu  Lys  Ala  Val  Ser  Lys  Glu  Met  Ser  Lys  Arg  Ser  Pro
 65                       70                   75
```

(2) INFORMATION FOR SEQ ID NO:7:

(i) SEQUENCE CHARACTERISTICS:
        (A) LENGTH: 21 amino acids
        (B) TYPE: amino acid
        (C) STRANDEDNESS: single
        (D) TOPOLOGY: linear (ix) SEQUENCE DESCRIPTION: SEQ ID NO:7:

```
Met  Val  Pro  Leu  Ser  Arg  Thr  Val  Arg  Xaa  Thr  Xaa  Ile  Ser  Ile
 1              5                   10                       15

Ser  Asn  Gln  Pro  Val  Asn
              20
```

(2) INFORMATION FOR SEQ ID NO:8:

(i) SEQUENCE CHARACTERISTICS:
        (A) LENGTH: 78 amino acid residues
        (B) TYPE: amino acids
        (C) STRANDEDNESS: single
        (D) TOPOLOGY: linear (ix) SEQUENCE DESCRIPTION: SEQ ID NO:8:

```
Met  Val  Pro  Leu  Ser  Arg  Thr  Val  Arg  Cys  Thr  Cys  Ile  Ser  Ile  Ser
 1              5                   10                       15

Asn  Gln  Pro  Val  Asn  Pro  Arg  Ser  Leu  Glu  Lys  Leu  Glu  Ile  Ile  Pro
              20                   25                       30

Ala  Ser  Gln  Phe  Cys  Pro  Arg  Val  Glu  Ile  Ile  Ala  Thr  Met  Lys  Lys
              35                   40                       45

Lys  Gly  Glu  Lys  Arg  Cys  Leu  Asn  Pro  Glu  Ser  Lys  Ala  Ile  Lys  Asn
         50                        55                  60

Leu  Leu  Lys  Ala  Val  Ser  Lys  Glu  Met  Ser  Lys  Arg  Ser  Pro
 65                       70                   75
```

(2) INFORMATION FOR SEQ ID NO:9:

(i) SEQUENCE CHARACTERISTICS:
        (A) LENGTH: 57 amino acid residues
        (B) TYPE: amino acids
        (C) STRANDEDNESS: single
        (D) TOPOLOGY: linear (ix) SEQUENCE DESCRIPTION: SEQ ID NO:9:

```
Met  Val  Pro  Leu  Ser  Arg  Thr  Val  Arg  Cys  Thr  Cys  Ile  Ser  Ile  Ser
 1              5                   10                       15

Asn  Gln  Pro  Val  Asn  Pro  Arg  Ser  Leu  Glu  Lys  Leu  Glu  Ile  Ile  Pro
              20                   25                       30
```

```
Ala  Ser  Gln  Phe  Cys  Pro  Arg  Val  Glu  Ile  Ile  Ala  Thr  Met  Lys  Lys
          35                       40                      45

Lys  Gly  Glu  Lys  Arg  Cys  Leu  Asn  Pro
          50                       55
```